(12) United States Patent
Robinson et al.

(10) Patent No.: US 10,933,150 B1
(45) Date of Patent: Mar. 2, 2021

(54) CONVEYOR BELT STERILIZATION APPARATUS AND METHOD

(71) Applicant: KlenLite, LLC, Lindon, UT (US)

(72) Inventors: Scott David Robinson, South Jordan, UT (US); Jeremiah Dean Brown, Heber City, UT (US)

(73) Assignee: KlenLite, LLC, Lindon, UT (US)

( * ) Notice: Subject to any disclaimer, the term of this patent is extended or adjusted under 35 U.S.C. 154(b) by 0 days.

(21) Appl. No.: 16/949,025

(22) Filed: Oct. 9, 2020

Related U.S. Application Data (60) Provisional application No. 62/706,213, filed on Aug. 5, 2020, provisional application No. 63/013,486, filed on Apr. 21, 2020.

(51) Int. Cl.
*A61L 2/10* (2006.01)
*B65G 45/10* (2006.01)
*A47F 9/04* (2006.01)

(52) U.S. Cl.
CPC ............. *A61L 2/10* (2013.01); *B65G 45/10* (2013.01); *A47F 9/04* (2013.01); *A47F 2009/041* (2013.01); *A61L 2202/11* (2013.01); *A61L 2202/14* (2013.01); *B65G 2203/0266* (2013.01); *B65G 2203/044* (2013.01)

(58) Field of Classification Search
CPC ............. B65G 45/10; B65G 45/24; B65G 2203/0266; B65G 2203/044; A47F 9/04; A47F 2009/041; A61L 2/10; A61L 2202/11; A61L 2202/14
USPC .......................................................... 198/494
See application file for complete search history.

(56) References Cited

U.S. PATENT DOCUMENTS

| | | | | |
|---|---|---|---|---|
| 4,274,509 A | * | 6/1981 | Thomson | F16N 27/00 184/15.3 |
| 5,248,027 A | * | 9/1993 | Kluger | B65G 39/16 198/502.4 |
| 6,894,299 B2 | | 5/2005 | Harrell et al. | |
| 7,160,566 B2 | | 1/2007 | Fink et al. | |
| 8,297,435 B2 | * | 10/2012 | Lathem | A61L 2/10 198/617 |
| 8,624,203 B2 | * | 1/2014 | Tullo | A61L 2/10 250/492.1 |
| 2004/0056201 A1 | * | 3/2004 | Fink | A23L 3/28 250/352 |
| 2004/0175290 A1 | | 9/2004 | Scheir et al. | |
| 2007/0059410 A1 | | 3/2007 | Steffen | |
| 2009/0159396 A1 | * | 6/2009 | Wood | B65G 41/005 198/318 |
| 2009/0252646 A1 | | 10/2009 | Holden et al. | |
| 2010/0243410 A1 | * | 9/2010 | Hall | B65G 45/22 198/495 |

(Continued)

FOREIGN PATENT DOCUMENTS

| | | |
|---|---|---|
| CN | 203638215 U | 6/2014 |
| CN | 104874006 A | 9/2015 |

(Continued)

*Primary Examiner* — Gene O Crawford
*Assistant Examiner* — Keith R Campbell
(74) *Attorney, Agent, or Firm* — Barnes & Thornburg LLP (57) ABSTRACT

A conveyor belt sanitization apparatus and method are provided for sanitizing a conveyor belt of the species commonly found at grocery stores and supermarkets using ultraviolet (UV) light. One or more UV light bulbs in the apparatus may be positioned to effectively sanitize a conveyor belt.

24 Claims, 6 Drawing Sheets

(56) References Cited

U.S. PATENT DOCUMENTS

| | | | |
|---|---|---|---|
| 2011/0158862 A1* | 6/2011 | Kim | B66B 31/02 422/292 |
| 2011/0308917 A1 | 12/2011 | Lathem | |
| 2012/0141322 A1 | 6/2012 | Fogg | |
| 2020/0289687 A1* | 9/2020 | Riley | A47F 9/04 |

FOREIGN PATENT DOCUMENTS

| | | | |
|---|---|---|---|
| CN | 107509795 | A | 12/2017 |
| CN | 107858816 | A | 3/2018 |
| CN | 107899039 | A | 4/2018 |
| CN | 108725908 | A | 11/2018 |
| CN | 209624562 | U | 11/2019 |
| CN | 210480276 | U | 5/2020 |
| EP | 3103741 | B1 | 12/2019 |
| KR | 200406332 | Y1 | 1/2006 |
| KR | 20140013609 | A | 2/2014 |

\* cited by examiner

CONVEYOR BELT STERILIZATION APPARATUS AND METHOD

RELATED APPLICATIONS

This application is a U.S. non-provisional application, which claims priority under 35 U.S.C. 120 and 119(e) to U.S. provisional application No. 63/013,486, filed Apr. 21, 2020 and to U.S. provisional application No. 62/706,213, filed Aug. 5, 2020. The disclosure of these priority applications are incorporated herein in their entirety, by this reference.

BACKGROUND

1. Field of the Invention

This invention relates to sterilizing surfaces, and more particularly relates to an apparatus and method of sterilizing a conveyor belt.

2. Description of the Related Art

Viral outbreaks of SARS-CoV-2, SARS, Ebola, MERS, and H1N1 have increased the public's awareness of contaminated surfaces. Commonly-shared hard surfaces may collect a contagion, such as a virus, and facilitate transmittal of the contagion from one carrier to others.

Examples of commonly shared surfaces include gas pump handles, door handles, and conveyor belts such as those found in consumer checkout stations at grocery stores. Consumers who carry a contagion may place their hands, or place packaged items contaminated with viral particles or bacteria on the conveyor belt and transmit the contagion to others. Clerks at the grocery store can use sanitary wipes or spray cleaning fluids with disinfectants onto the conveyors, but such activities interrupt the clerk's work flow and can be messy. Thus, there remains a need in the art for sanitizing conveyor belt systems, especially in stores handling consumer goods and groceries.

BRIEF SUMMARY

From the foregoing discussion, it should be apparent that a need exists for an apparatus and method adapted to sanitize a conveyor belt. Beneficially, such an apparatus and method would use ultraviolet light (UV) to disinfect a conveyor belt facilitating sanitization.

A conveyor belt sanitization apparatus is provided. The apparatus includes a housing defining an interior cavity; and an UV light source coupled to the housing in the interior cavity.

In some aspects, a conveyor belt sanitization apparatus includes a first endcap coupled to a first end of the housing, a second endcap coupled to a second end of the housing, a first mounting bracket coupled to the first endcap, and a second mounting bracket coupled to the second endcap.

In some aspects, a conveyor belt sanitization apparatus includes an inner housing positioned in the interior cavity and between the UV light source and the housing.

In some aspects, the conveyor belt sanitization apparatus includes a sensor mounted on the housing or on the inner housing. In some embodiments, the sensor is an optical encoder.

In some aspects, the conveyor belt sanitization apparatus includes a printed circuit board attached to the housing in the interior cavity or attached to the inner housing.

In some aspects, the conveyor belt sanitization apparatus includes a ballast positioned between the inner housing and housing in the interior cavity. In some embodiments, the ballast is an electrical ballast.

In some aspects, the UV light source comprises one or a plurality of UV germicidal bulbs.

In some aspects, the conveyor belt sanitization apparatus includes a second sensor to detect presence of a liquid.

In some aspects, the conveyor belt sanitization apparatus includes an external fuse positioned between a power supply and a printed circuit board.

In some aspects, the conveyor belt sanitization apparatus includes a safe-guard extending along an edge of the housing adapted to prevent objects from passing underneath the conveyor belt sanitization apparatus.

A conveyor belt sanitization system is also provided. The system includes a conveyor belt adapted to rotate on a plurality of rollers; a conveyor belt sanitization apparatus comprising a housing defining an interior cavity and an open bottom end; and a UV light source coupled to the housing in the interior cavity, the UV light source adapted to emit UV light onto the conveyor belt through the open bottom end; and a mounting bracket adapted to detachably affix the conveyor belt sanitization apparatus in close proximity to the conveyor belt.

In some aspects, the conveyor belt sanitization apparatus is positioned within about 5 centimeters of the conveyor belt.

In some aspects, the conveyor belt sanitization apparatus is positioned within about 8 millimeters of the conveyor belt.

In some aspects, the conveyor belt sanitization apparatus further comprises a sensor and a controller to switch on the UV light when the conveyor belt moves.

In some aspects, the conveyor belt sanitization apparatus is positioned above or below the conveyor belt.

In some aspects, the conveyor belt sanitization apparatus is positioned before or after a product scanner.

A method of sanitizing a conveyor belt is provided. The method includes passing the conveyor belt in proximity to a conveyor belt sanitization apparatus. The apparatus includes a housing defining an interior cavity and an open bottom end; and an ultraviolet (UV) light source coupled to the housing in the interior cavity, the UV light source adapted to emit UV light onto the conveyor belt through the open bottom end. The method includes emitting UV light onto the conveyor belt; detecting movement of the conveyor belt using a sensor positioned on the conveyor belt sanitization apparatus; and switching off the UV light when the conveyor belt is stationary and switching on the UV light when the conveyor belt is in motion.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE SEVERAL VIEWS OF THE DRAWINGS

A detailed description of the invention is hereafter described with specific reference being made to the drawings in which.

DETAILED DESCRIPTION

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The schematic flow chart diagrams included herein are generally set forth as logical flow chart diagrams. As such, the depicted order and labeled steps are indicative of one aspect of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

A conveyor belt sanitization apparatus is provided. The apparatus includes a housing defining an interior cavity; and an UV light source coupled to the housing in the interior cavity.

Figure 4:
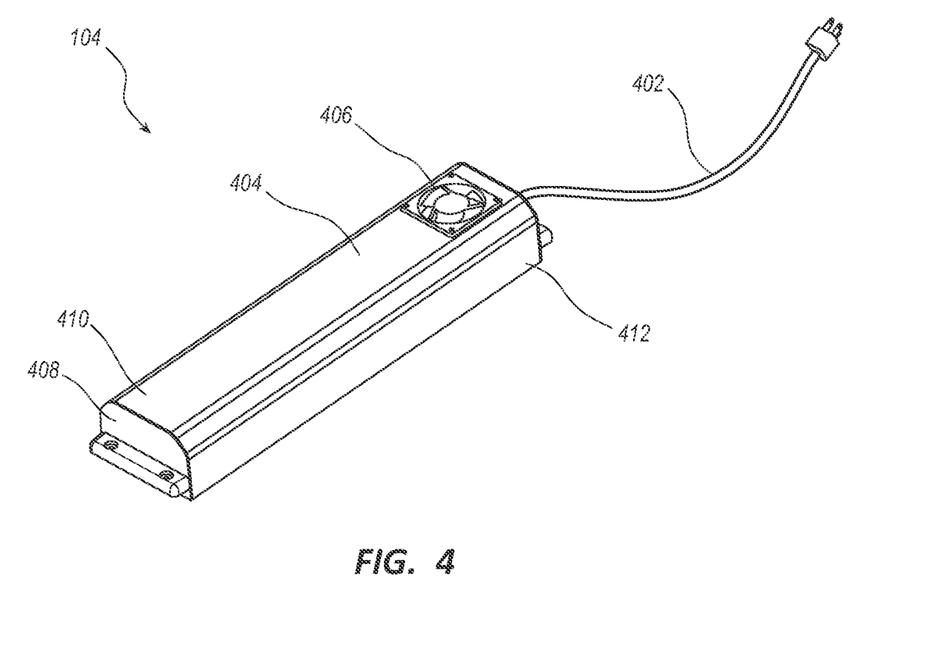
FIG. 4 is a perspective view illustrating one aspect of the conveyor belt sanitization apparatus.
Figure 5:
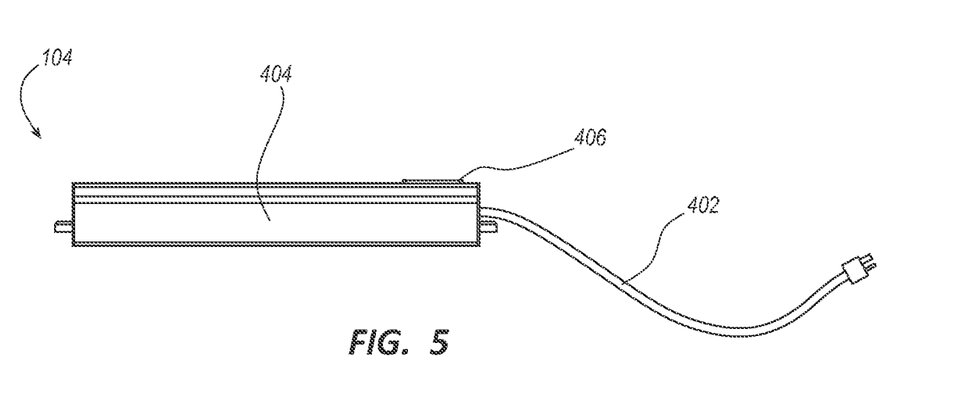
FIG. 5 is a perspective view illustrating one aspect of the conveyor belt sanitization apparatus.

FIGS. 4-8 show various aspects of the apparatus. FIG. 4 shows an embodiment of the apparatus 104 that comprises a housing 404 adapted to shield an ultraviolet bulb which emits UV light onto the conveyor belt when switched on. The housing 404 includes a first end 410 and a second end 412. An endcap 408 may be attached to each of the first end 410 and the second end 412. A power cord 402 is connected to the UV light source inside the housing 404. The apparatus may also include a fan 406 for cooling the UV light source.

Figure 6:
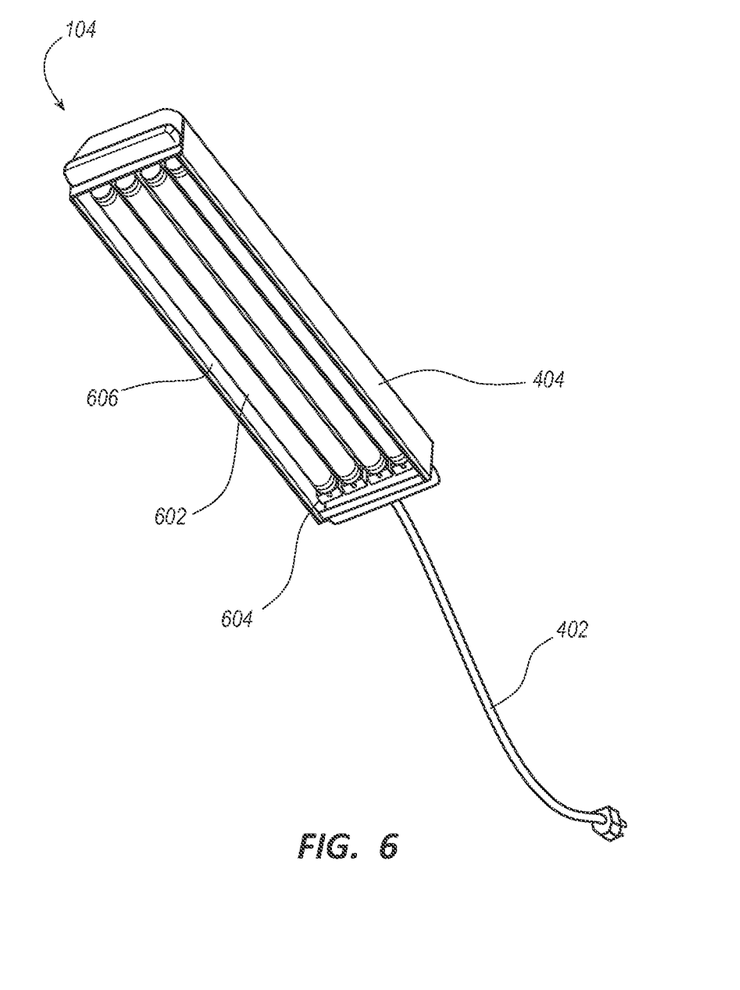
FIG. 6 is a lower perspective view illustrating one aspect of the conveyor belt sanitization apparatus.

FIG. 6 shows a lower perspective view of an embodiment of the apparatus 104. The housing 404 defines an interior cavity 606 in which UV bulbs 602 can be positioned. Bulb holders 604 attached to the housing position the bulbs 602 within the housing 404.

Figure 7:
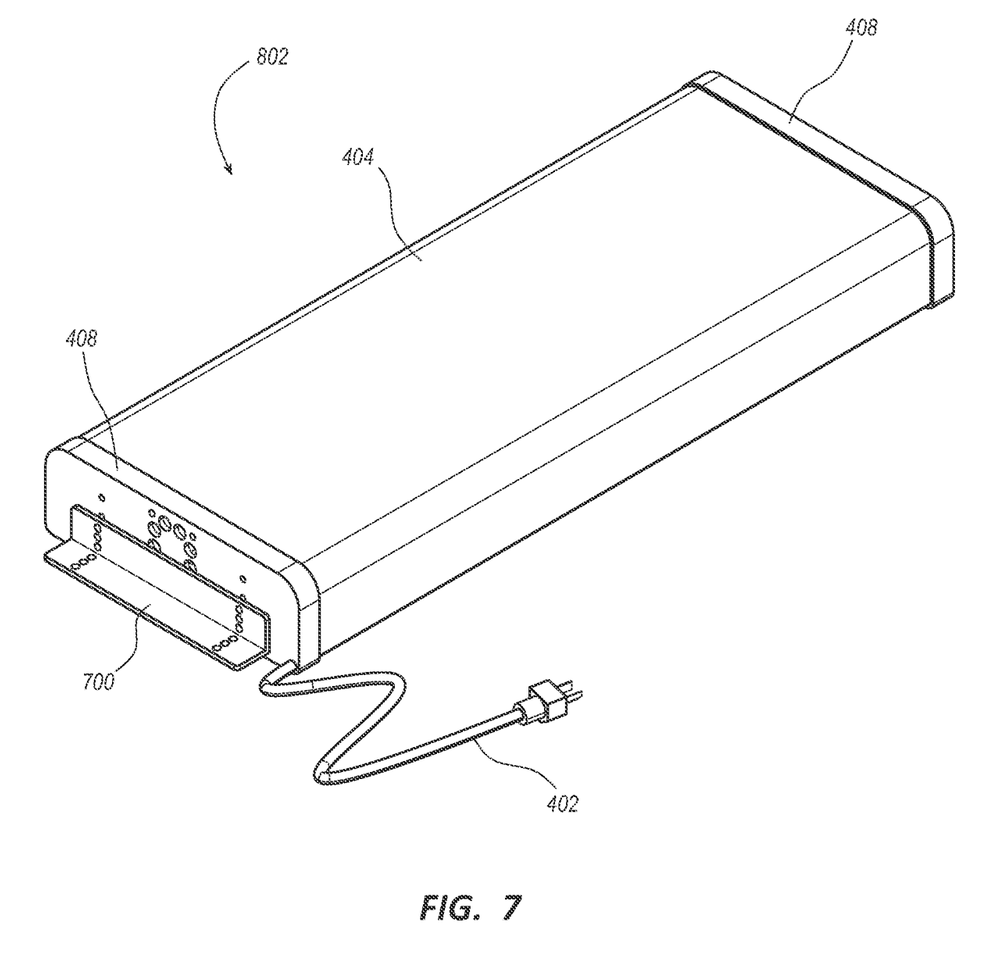
FIG. 7 is a perspective view illustrating one aspect of the conveyor belt sanitization apparatus.

FIG. 7 shows an embodiment of the apparatus 802 where a bracket 700 is attached to an endcap 408. The bracket 700 can be attached to a support structure of a conveyor belt.

Figure 8:
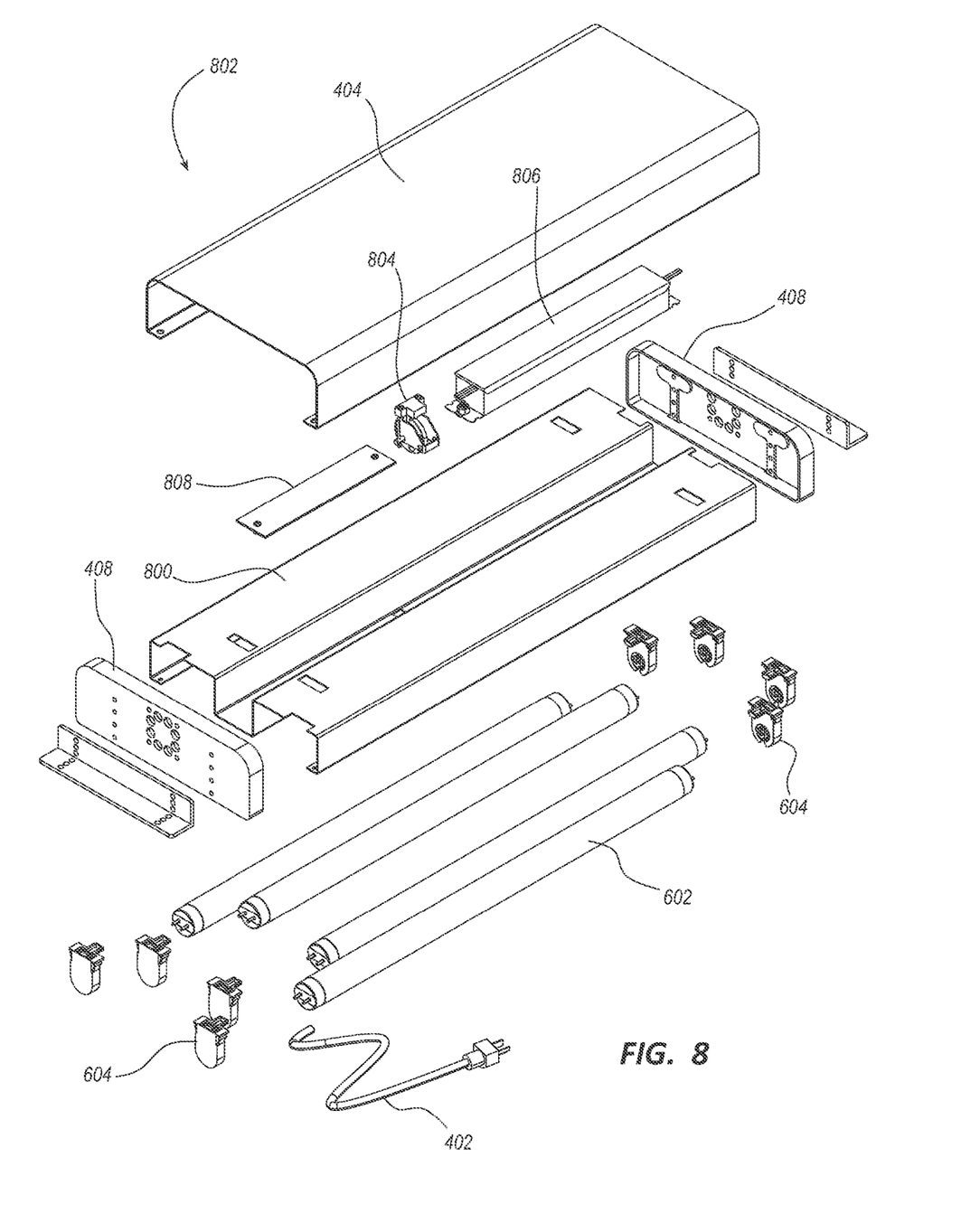
FIG. 8 is an exploded view of the conveyor belt sanitization apparatus.

FIG. 8 shows an exploded view of the apparatus. The housing 404 may include within an interior cavity of the housing 404 an inner housing 800. On the inner housing 800, a sensor 804 may be attached along with a circuit board 808. Between the housing 404 and the inner housing 800, a ballast 806 may be positioned. UV bulbs 602 removably attach to the bulb holders 604 within a cavity of the inner housing 800.

The location of the sensor is not particularly limited. For example, the sensor may be mounted on the housing or on the inner housing. In some aspects, the apparatus may include multiple sensors. A sensor may detect if the apparatus has been dislodged and communicate to a controller to prevent the UV bulbs from turning on and exposing nearby persons to UV light. The sensor may also detect movement of the conveyor belt. For example, when the conveyor belt is stationary the UV light may be switched off, but when the belt starts moving, the sensor may detect movement, send a signal to a controller, and switch on the UV light.

The sensor may be operably connected to the circuit board to communicate conveyor motion data or apparatus position to the circuit board having a controller.

In some aspects, the conveyor belt sanitization apparatus may include more than one sensor. For example, the apparatus may include a second sensor to detect presence of a liquid. This sensor may be positioned on the apparatus where contact with liquids is likely to occur. Additional safety features may be included in the apparatus such as an external fuse positioned between a power supply and a printed circuit board.

In some aspects, the conveyor belt sanitization apparatus is positioned above a conveyor belt with a distance of a few millimeters between the apparatus and the belt. To prevent objects from passing between the conveyor belt sanitization apparatus the conveyor belt, the housing of the apparatus may include a safe-guard extending along an edge of the housing.

In some aspects, the conveyor belt sanitization apparatus includes a ballast positioned between the inner housing and housing in the interior cavity. The ballast may be an electrical ballast that is operably connected to the circuit board.

In some aspects, the UV light source comprises a plurality of UV germicidal bulbs. The UV germicidal bulbs may produce ultraviolet C (UVC) light to inactivate bacteria, viruses, and protozoa.

The UV light source, in some embodiments, may be varied in intensity or lux. In some embodiments, the apparatus may be configured to allow selection of the fixed spectrum of UV light emitted upon the conveyor belt adapted to maximize disinfectant effectiveness. In other aspects, the lux of the light bulb may be adjusted by selectively adjusting the power output to the light bulb. In some aspects, the UV light source may be one or a plurality of UVC light emitting diodes. In some aspects, the apparatus may include a reset button for resetting the lamp change timer.

In some aspects, the apparatus may include an indicator. The indicator can be an LED light or other light indicator to indicate that the device is on, malfunctioning, or that a UV light source is burnt out or nearing end of life. There may be multiple indicators that alert users of different conditions of the apparatus, for example, the apparatus may include a light for indicating power and a second light for indicating the condition of the UV light source.

The power supply is not particularly limited. For example, the apparatus can be adapted to run on any available power supply such as 230 V or 120 V.

Figure 1:
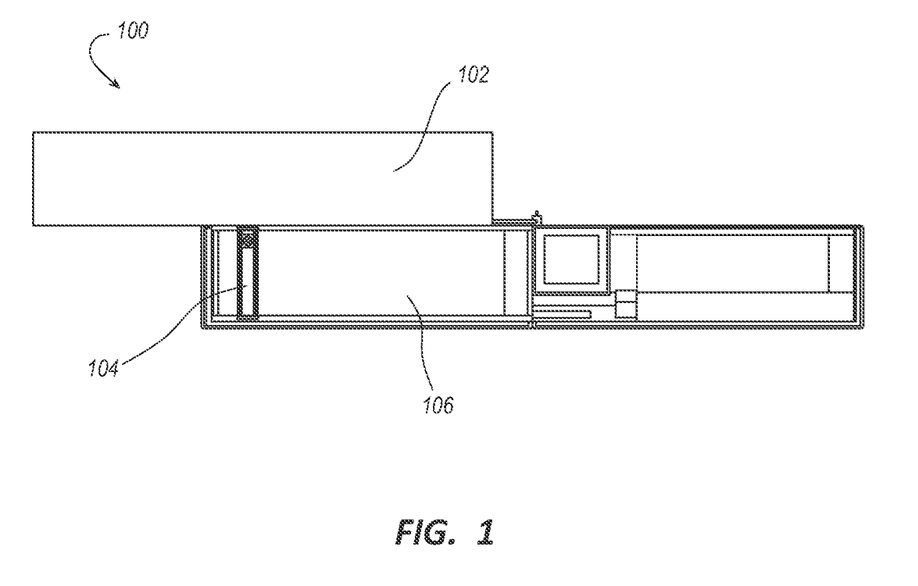
FIG. 1 shows a top perspective view illustrating one aspect of a conveyor belt sterilization system.
Figure 2:
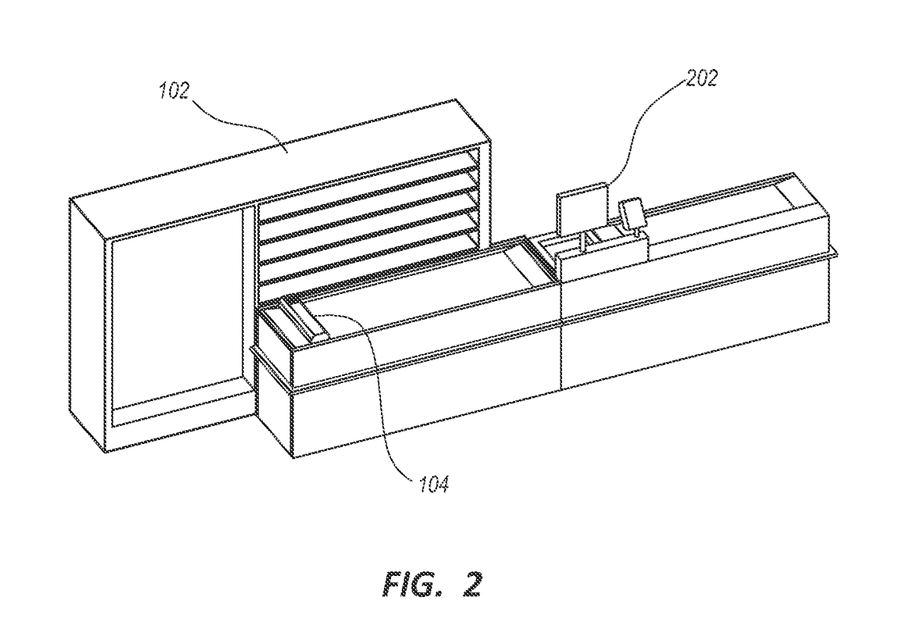
FIG. 2 is a perspective view illustrating one aspect of a conveyor belt sterilization system.
Figure 3:
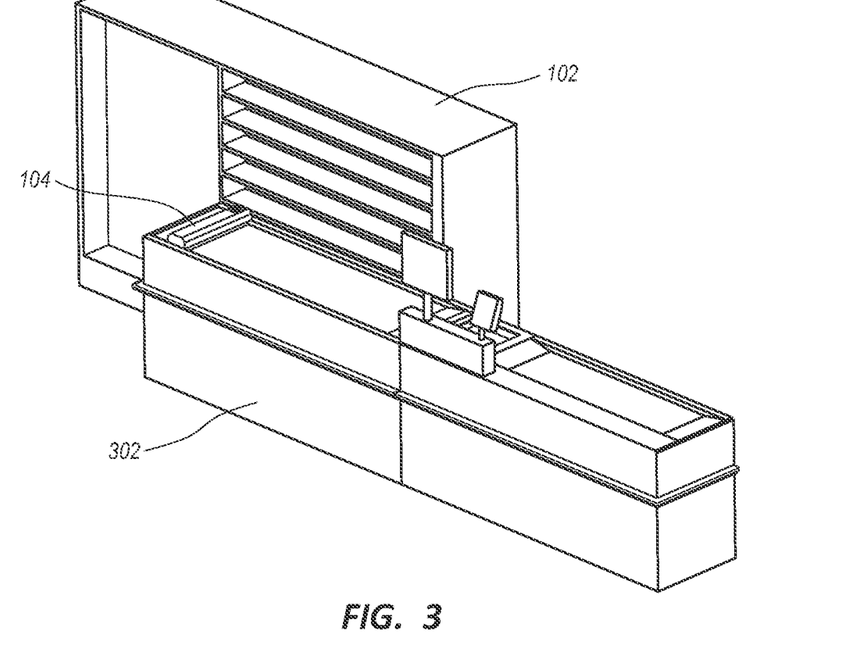
FIG. 3 is a side perspective view illustrating one aspect of a conveyor belt sterilization system.

FIG. 1-3 illustrate perspective views of a conveyor belt sterilization system 100. Shelves 102 may be positioned adjacent the conveyor belt 106. An apparatus 104 is detachably affixed in close proximity to the conveyor belt 106. The apparatus 104, in the shown embodiment, positions above a roller adapted to rotate the conveyor belt 106 on its top surface toward a cashier standing in front of a registrar 202.

The apparatus 104 may be detachably affixed to the structure supporting the conveyor belt 106 using means known to those of skill in the art, including fastening means such as bolts or screws, mounted on a stand or mounting bracket, or formed with the structure 302 as a single integrated piece.

In some aspects, the conveyor belt sanitization apparatus is positioned within about 5 centimeters of the conveyor belt. In some aspects, the conveyor belt sanitization apparatus is positioned within about 8 millimeters of the conveyor belt. The apparatus may also include a barrier positioned on the outside of the housing to prevent items from inserting between the apparatus and the conveyor belt.

In various aspects, the apparatus is adapted to be switched on automatically when a cashier activates the conveyor belt itself. In other aspects, the apparatus is positioned beneath the conveyor belt out of sight, or is used in connection with a liquid-dispensing system comprising nozzles adapted to dispense liquid onto the belt. In these aspects, the belt is first exposed to UV light on rotation and then to liquid disinfectant. The liquid disinfectant may be applied and removed by rollers integrated into the belt structure to rotate the belt.

A plurality of apparatuses and light bulbs may be positioned around the conveyor belt. In various aspects, UV light is additionally or alternatively adapted to illuminate a scanning area disposed at a terminal end of the conveyor belt where perishable foods and other items are scanned.

A method of sanitizing a conveyor belt is provided. The method includes passing the conveyor belt in proximity to a conveyor belt sanitization apparatus. The method includes emitting UV light onto the conveyor belt; detecting movement of the conveyor belt using a sensor positioned on the conveyor belt sanitization apparatus; and switching off the UV light when the conveyor belt is stationary and switching on the UV light when the conveyor belt is in motion.

Figure 9:
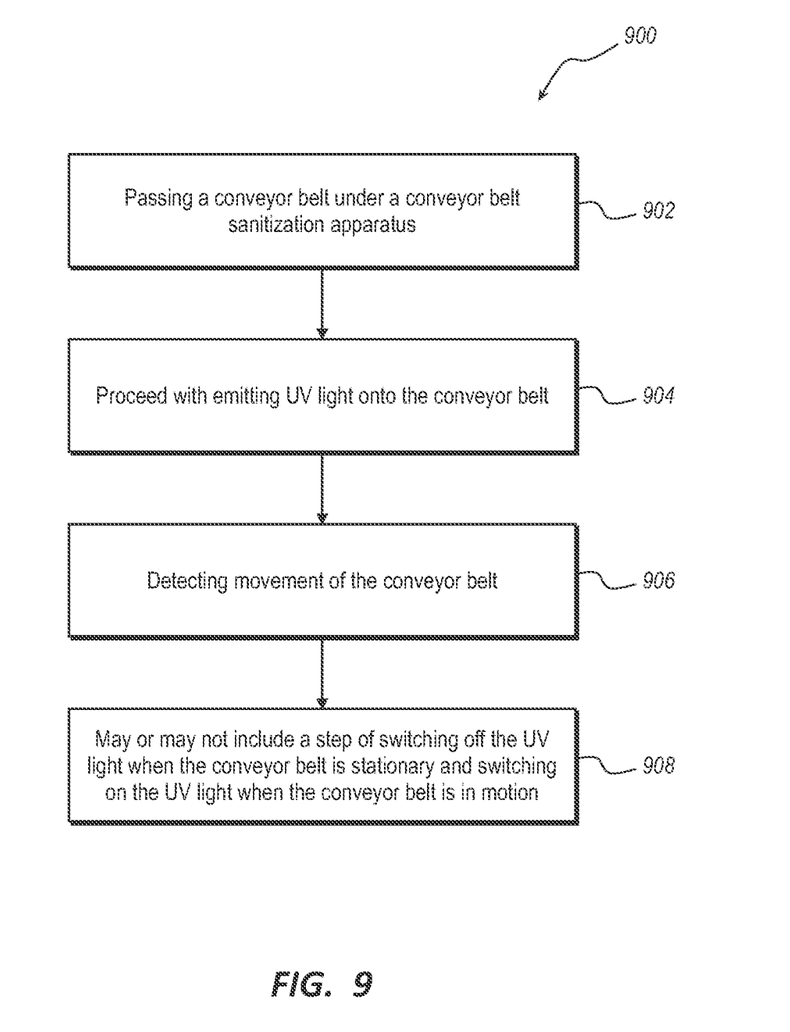
FIG. 9 is a flow chart illustrating one method of sterilizing a conveyor belt.

FIG. 9 shows a flow chart illustrating one method 900 of sterilizing a conveyor belt. The method 900 begins by passing a conveyor belt under a conveyor belt sanitization apparatus 902. The method proceeds with emitting UV light onto the conveyor belt 904 and detecting movement of the conveyor belt 906. Finally, the method may include the step of switching off the UV light when the conveyor belt is stationary and switching on the UV light when the conveyor belt is in motion 908. The steps of the method 900 may be executed in any order.

In certain embodiments, the system includes a monitoring and controlling unit that comprises a controller and a plurality of sensors. Each of the plurality of sensors can be in communication with the controller. For example, if the unit comprises two sensors, each of the two sensors can be in communication with the controller. In some embodiments, the controller can be attached to the housing.

The position of the conveyor belt sanitization apparatus is not limited to above the conveyor belt. In some aspects, the system may include a conveyor belt sanitization apparatus positioned above or below the conveyor belt. Also, the conveyor belt sanitization apparatus is positioned before or after a product scanner.

As used herein, the term "controller" refers to a manual operator or an electronic device having components, such as a processor, memory device, digital storage medium, a communication interface including communication circuitry operable to support communications across any number of communication protocols and/or networks, a user interface (e.g., a graphical user interface that may include cathode ray tube, liquid crystal display, plasma display, touch screen, or other monitor), and/or other components.

The controller is preferably operable for integration with one or more application-specific integrated circuits, programs, computer-executable instructions or algorithms, one or more hard-wired devices, wireless devices, and/or one or more mechanical devices. Moreover, the controller is operable to integrate the feedback, feed-forward, and/or predictive loop(s) of the invention. Some or all of the controller system functions may be at a central location, such as a network server, for communication over a local area network, wide area network, wireless network, internet connection, microwave link, infrared link, wired network (e.g., Ethernet) and the like. In addition, other components, such as a signal conditioner or system monitor, may be included to facilitate signal transmission and signal-processing algorithms.

In certain aspects, the controller includes hierarchy logic to prioritize any measured or predicted properties associated with system parameters. For example, the controller may be programmed to prioritize apparatus position over conveyor belt movement. It should be appreciated that the object of such hierarchy logic is to allow improved control over the system parameters and to avoid circular control loops.

In some embodiments, the monitoring and controlling unit and method associated therewith includes an automated controller. In some embodiments, the controller is manual or semi-manual.

Preset parameters or programs are entered into the controller or remote device so that the controller or remote device can determine if a measured property is outside of an acceptable range. Based on the information received by the plurality of sensors, the controller or remote device can make appropriate adjustments or send out an appropriate alert.

In certain embodiments, the remote device or controller can include appropriate software to receive data from the plurality of sensors and determine if the data indicates that one or more measured parameters are within, or outside, an acceptable range. The software can also allow the controller to determine appropriate actions that should be taken to remedy the parameters that is outside of the acceptable range.

The monitoring and controlling system and/or controller disclosed herein can incorporate programming logic to convert analyzer signals from the plurality of sensors to pump adjustment logic and, in certain embodiments, control one or more of a plurality of UV bulbs.

The sensors disclosed herein are operable to sense and/or predict a property associated with the apparatus and convert the property into an input signal, e.g., an electric signal, capable of being transmitted to the controller. A transmitter associated with each sensor transmits the input signal to the controller. The controller is operable to receive the transmitted input signal, convert the received input signal into an input numerical value, analyze the input numerical value to determine if the input numerical value is within an optimum range, generate an output numerical value, convert the output numerical value into an output signal, e.g., an electrical signal, and transmit the output signal to a receiver.

Data transmission of measured parameters or signals to chemical pumps, alarms, remote monitoring devices, such as computers or cellular telephones, or other system components is accomplished using any suitable device, and across any number of wired and/or wireless networks, including as examples, WiFi, WiMAX, Ethernet, cable, digital subscriber line, Bluetooth, cellular technologies (e.g., 2G, 3G, Universal Mobile Telecommunications System (UMTS), GSM, Long Term Evolution (LTE), or more) etc. Any suitable interface standard(s), such as an Ethernet interface, wireless interface (e.g., IEEE 802.11a/b/g/x, 802.16, Bluetooth, optical, infrared, radiofrequency, etc.), universal serial bus, telephone network, the like, and combinations of such interfaces/connections may be used.

As used herein, the term "network" encompasses all of these data transmission methods. Any of the described devices (e.g., archiving systems, data analysis stations, data capturing devices, process devices, remote monitoring devices, chemical injection pumps, etc.) may be connected to one another using the above-described or other suitable interface or connection.

In some embodiments, system parameter information is received from the system and archived. In certain embodiments, system parameter information is processed according to a timetable or schedule. In some embodiments, system parameter information is immediately processed in real-time or substantially real-time.

While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a device" is intended to include "at least one device" or "one or more devices."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

The transitional phrase "comprising," which is synonymous with "including," "containing," or "characterized by," is inclusive or open-ended and does not exclude additional, un-recited elements, components, ingredients and/or method steps.

As used herein, the term "about" refers to the cited value being within the errors arising from the standard deviation found in their respective testing measurements, and if those errors cannot be determined, then "about" may refer to, for example, within 5% of the cited value.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is, therefore, intended that such changes and modifications be covered by the appended claims.

What is claimed is:

1. A conveyor belt sanitization apparatus, the apparatus comprising:
   a housing defining an interior cavity;
   an ultraviolet (UV) light source coupled to the housing in the interior cavity;
   a sensor mounted on the housing or on an inner housing for detecting motion;
   a first endcap coupled to a first end of the housing;
   a second endcap coupled to a second end of the housing;
   a first mounting bracket coupled to the first endcap; and
   a second mounting bracket coupled to the second endcap.

2. The apparatus of claim 1, wherein the inner housing positioned in the interior cavity and between the UV light source and the housing.

3. The apparatus of claim 1, wherein the sensor is an optical encoder.

4. The apparatus of claim 1, further comprising a printed circuit board attached to the housing in the interior cavity or attached to the inner housing.

5. The apparatus of claim 2, further comprising a ballast positioned between the inner housing and housing in the interior cavity.

6. The apparatus of claim 5, wherein the ballast is an electrical ballast.

7. The apparatus of claim 1, wherein the UV light source comprises a plurality of UV germicidal bulbs.

8. The apparatus of claim 1, further comprising a second sensor to detect presence of a liquid.

9. The apparatus of claim 1, further comprising an external fuse positioned between a power supply and a printed circuit board.

10. The apparatus of claim 1, further comprising a safeguard extending along an edge of the housing adapted to prevent objects from passing underneath the conveyor belt sanitization apparatus.

11. A conveyor belt sanitization system, the system comprising:
    a conveyor belt;
    a conveyor belt sanitization apparatus comprising a housing defining an interior cavity and an open bottom end; an ultraviolet (UV) light source coupled to the housing in the interior cavity, the UV light source adapted to emit UV light onto the conveyor belt through the open bottom end, an inner housing positioned in the interior cavity and between the UV light source and the housing; and a ballast positioned between the inner housing and housing in the interior cavity; and
    a mounting bracket adapted to detachably affix the conveyor belt sanitization apparatus in close proximity to the conveyor belt.

12. The system of claim 11, wherein the conveyor belt sanitization apparatus is positioned within about 8 centimeters of the conveyor belt.

13. The system of claim 11, wherein the conveyor belt sanitization apparatus is positioned within about 5 millimeters of the conveyor belt.

14. The system of claim 11, wherein the conveyor belt sanitization apparatus further comprises a sensor and a controller to switch on the UV light source when the conveyor belt moves.

15. The system of claim 14, wherein the sensor is an optical encoder.

16. The system of claim 11, wherein the conveyor belt sanitization apparatus is positioned above or below the conveyor belt.

17. The system of claim 11, wherein the conveyor belt sanitization apparatus is positioned before or after a product scanner.

18. A method of sanitizing a conveyor belt, comprising:
passing the conveyor belt in proximity to a conveyor belt sanitization apparatus comprising a housing defining an interior cavity and an open bottom end; and an ultraviolet (UV) light source coupled to the housing in the interior cavity, the UV light source adapted to emit UV light onto the conveyor belt through the open bottom end, an inner housing positioned in the interior cavity and between the UV light source and the housing; and a ballast positioned between the inner housing and housing in the interior cavity;
emitting UV light onto the conveyor belt;
detecting movement of the conveyor belt using a sensor positioned on the conveyor belt sanitization apparatus; and
switching off the UV light when the conveyor belt is stationary and switching on the UV light when the conveyor belt is in motion.

19. A conveyor belt sanitization apparatus, the apparatus comprising:
a housing defining an interior cavity;
an ultraviolet (UV) light source coupled to the housing in the interior cavity;
a sensor mounted on the housing or on an inner housing for detecting motion, the inner housing being positioned in the interior cavity and between the UV light source and the housing; and
a ballast positioned between the inner housing and housing in the interior cavity.

20. The apparatus of claim 19, wherein the ballast is an electrical ballast.

21. The apparatus of claim 19, wherein the UV light source comprises a plurality of UV germicidal bulbs.

22. The apparatus of claim 19, further comprising a second sensor to detect presence of a liquid.

23. The apparatus of claim 19, further comprising an external fuse positioned between a power supply and a printed circuit board.

24. The apparatus of claim 19, further comprising a safe-guard extending along an edge of the housing adapted to prevent objects from passing underneath the conveyor belt sanitization apparatus.

* * * * *